United States Patent
Knauf et al.

(10) Patent No.: US 9,416,094 B2
(45) Date of Patent: Aug. 16, 2016

(54) PROCESS FOR THE PREPARATION OF DI- AND POLYAMINES OF THE DIPHENYLMETHANE SERIES

(71) Applicant: Covestro Deutschland AG, Leverkusen (DE)

(72) Inventors: Thomas Knauf, Dormagen (DE); Wolfgang Lorenz, Dormagen (DE); Stefan Wershofen, Monchengladbach (DE); Richard Adamson, Leichlingen (DE); Karsten Becker, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 14/783,163

(22) PCT Filed: Apr. 8, 2014

(86) PCT No.: PCT/EP2014/056979
§ 371 (c)(1),
(2) Date: Oct. 8, 2015

(87) PCT Pub. No.: WO2014/166901
PCT Pub. Date: Oct. 16, 2014

(65) Prior Publication Data
US 2016/0068473 A1    Mar. 10, 2016

(30) Foreign Application Priority Data
Apr. 11, 2013 (EP) ..................................... 13163357

(51) Int. Cl.
*C07C 209/78* (2006.01)
*C07C 263/10* (2006.01)

(52) U.S. Cl.
CPC .............. *C07C 209/78* (2013.01); *C07C 263/10* (2013.01); *C07C 2101/16* (2013.01)

(58) Field of Classification Search
CPC .. C07C 209/60; C07C 209/86; C07C 209/78; C07C 209/68
See application file for complete search history.

(56) References Cited

U.S. PATENT DOCUMENTS

| | | | |
|---|---|---|---|
| 2,780,304 A | * | 2/1957 | Pew ........................ C10G 33/06 208/187 |
| 5,286,760 A | | 2/1994 | Bolton et al. |
| 6,433,219 B1 | | 8/2002 | Stroefer et al. |
| 6,576,788 B1 | | 6/2003 | Penzel et al. |
| 6,987,165 B2 | | 1/2006 | Auer et al. |
| 7,230,130 B2 | | 6/2007 | Strofer et al. |
| 7,253,321 B2 | | 8/2007 | Hagen et al. |
| 7,312,362 B2 | | 12/2007 | Keggenhoff et al. |
| 7,528,283 B2 | | 5/2009 | Pohl et al. |
| 2006/0094897 A1 | | 5/2006 | Muller et al. |
| 2009/0240077 A1 | * | 9/2009 | Wershofen ............ C07C 209/78 560/347 |
| 2013/0310616 A1 | | 11/2013 | Neumann et al. |

FOREIGN PATENT DOCUMENTS

| | | |
|---|---|---|
| DE | 844896 | 4/1944 |
| EP | 0451442 | 4/1990 |
| GB | 1517585 | 7/1978 |
| GB | 1517585 07-1978 | * 7/1978 |
| WO | 2008148631 | 12/2008 |

OTHER PUBLICATIONS

Muller et al, Ullman's Encyclopedia of Industrial Chemistry, Liquid-Liquid Extraction, 2013, 21,Wiley-VCH Verlag Gmbh & Co, HGaA, pp. 249-307.*
Twitchett, H.J., Chem. Soc. Rev. 3(2), p. 223 (1974).
Muller, E. et al., Ullmanns Encyclopedia of Industrial Chemistry, vol. 21, pp. 272-274, 2012, Wiley-VCH Verlag GmbH & Co., KGaA.
Kirk-Othmer Encyclopedia of Chemical Technology, Jun. 15, 2007, pp. 22-23.

* cited by examiner

*Primary Examiner* — Paul A Zucker
(74) *Attorney, Agent, or Firm* — Donald R. Palladino

(57) ABSTRACT

The invention relates to a method for producing diamines and polyamines of the diphenylmethane series in which, by using a coalescence auxiliary in the phase separation of the process product obtained in the scrubbing of the neutralized crude product, the fraction of water and thus also of water-soluble impurities in the organic MDA-containing phase is reduced. According to the invention, the coalescence auxiliary used is a filter bed made of coalescence fiber material. The di- and polyamines of the diphenylmethane series obtained after distillative purification of this MDA-containing organic phase are exceptionally suitable for the preparation of the corresponding isocyanates.

10 Claims, No Drawings

PROCESS FOR THE PREPARATION OF DI- AND POLYAMINES OF THE DIPHENYLMETHANE SERIES

CROSS-REFERENCE TO RELATED APPLICATIONS

This application is a National Phase Application of PCT/EP2014/056979, filed Apr. 8, 2014, which claims priority to European Application No.: 13163357.0, filed Apr. 11, 2013, each of which being incorporated herein by reference.

FIELD

The present invention relates to a process for the preparation of di- and polyamines of the diphenylmethane series in which, by using a coalescence auxiliary in the phase separation of the process product obtained in the washing of the neutralized crude product, the fraction of water and thus also of water-soluble impurities in the organic, MDA-containing phase is reduced. According to the invention, the coalescence auxiliary used is a filter bed made of coalescence fiber material. The di- and polyamines of the diphenylmethane series obtained after distillative purification of this MDA-containing organic phase are exceptionally suitable for the preparation of the corresponding isocyanates.

BACKGROUND

The preparation of di- and polyamines of the diphenylmethane series (MDA) by reaction of aniline with formaldehyde in the presence of acidic catalysts is generally known. For the purposes of the present invention, di- and polyamines of the diphenylmethane series are understood as meaning amines and mixtures of amines of the following type:

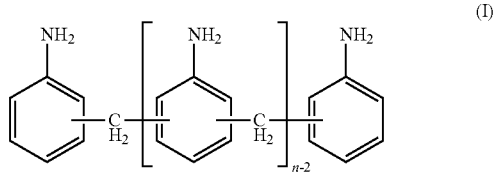

Here, n stands for a natural number $\geq 2$. Hereinbelow, the compounds of this type in which n=2 are referred to as diamines of the diphenylmethane series or diaminodiphenylmethanes (subsequently MMDA). Compounds of this type in which n>2 are referred to in the context of this invention as polyamines of the diphenylmethane series or polyphenylenepolymethylenepolyamines (subsequently PMDA). Mixtures of both types are referred to as di- and polyamines of the diphenylmethane series (subsequently MDA). The corresponding isocyanates, which can be derived formally from the compounds of the formula (I) by replacing all of the $NH_2$ groups with NCO groups, are accordingly referred to as diisocyanates of the diphenylmethane series (subsequently MMDI), polyisocyanates of the diphenylmethane series or polyphenylenepolymethylenepolyisocyanates (subsequently PMDI) or di- and polyisocyanates of the diphenylmethane series (subsequently MDI). The polymer (n>2) here is usually always present both in the case of the amine as well as in the case of the isocyanate in a mixture with the dimer (n=2), meaning that in practice only two compound types are relevant, the pure dimers (MMDA or MMDI) and the mixture of dimers and polymers (MDA or MDI).

Industrially, the di- and polyamine mixtures are converted to the corresponding di- and polyisocyanates of the diphenylmethane series predominantly by phosgenation. The continuous or partially discontinuous preparation of MDA is disclosed e.g. in U.S. Pat. No. 5,286,760, EP-A-451442 and WO-A-99/40059.

The work-up of the acidic reaction mixture obtained in the preparation is initiated according to the prior art by neutralization with a base. According to the prior art, the neutralization usually takes place at temperatures of, for example, 90° C. to 100° C. without the addition of further substances (H. J. Twitchett, Chem. Soc. Rev. 3(2), p. 223 (1974)). However, it can also take place on a different temperature level in order e.g. to increase the rate of the degradation of troublesome byproducts. Hydroxides of the alkali metal and alkaline earth metal elements are suitable as bases. Aqueous NaOH is preferably used.

After the neutralization, the organic phase is separated from the aqueous phase in a separating container. The crude-MDA-containing organic phase which remains after separating off the aqueous phase is subjected to further work-up steps, such as e.g. a washing with water (base washing), in order to wash residual salts from the crude MDA. Finally, the crude MDA purified in this way is freed from excess aniline, water and other substances present in the mixture (e.g. further solvents) by means of suitable processes such as e.g. distillation, extraction or crystallization. In particular, two-stage or multistage distillations can be used. In the case of vapor/liquid separation, in the preevaporation in the case of such a two-stage or multistage distillation, the entrainment of MDA-containing droplets into the vapor phase can be reduced by a process step known to the person skilled in the art for drop separation, e.g. by incorporating gravitational separators, centrifugal separators such as e.g. cyclones, impingement separators or baffle plate separators, such as e.g. lamella separators, fixed beds or packings for drop separation, knitted-fabric separators, Venturi separators or a combination of the aforementioned mechanisms. As is known from EP 1 813 598 B1, an increased MDA fraction in the feed aniline leads to quality losses in the MDA and MDI prepared therefrom.

In the same process step, aminic secondary components in the aniline, which may also originate from the aniline process itself and which have already been described in EP 2 103 595 A1, in particular the low-boiling unsaturated and/or substituted (cyclo)aliphatic primary, secondary or tertiary amines such as cyclohexylamine, N,N-dicyclohexylamine and N-methylcyclohexylamine, can be removed. This reduces the amount of HCl required in the protonation of the aminal because these secondary components can otherwise compete with aniline during the protonation and thus reduce the effective protonation.

The work-up customary according to the prior art is disclosed for example in EP 1 652 835 A1, page 3, line 58 to page 4, line 13 and EP 2 103 595 A1, page 7, line 21 to 37. EP 1 652 835 A1 teaches that the separation off of the aqueous phase from the product-containing organic phase after the neutralization and/or the subsequent washing can be very considerably impaired by the formation of a third phase (mulm or mulm layer). This third phase is a stable, sometimes voluminous intermediate phase which arises between the aqueous and the organic phase and hinders phase separation and, in extreme cases, even prevents it completely. In the worst case for operational progression, the phase separation container or containers have to be emptied completely and cleaned. The content of the phase separation container or containers then has to be laboriously worked up or disposed of, Which is associated with considerable costs. Under certain circumstances, this can also lead to the continuous production having to be interrupted. To solve this problem, the cited specification proposes a process in which the hydrochloric acid used as catalyst comprises less than 0.001 percent by weight of divalent and/or polyvalent metal ions.

The same problem is observed in WO 2008/148631 A1, it being proposed in this case to use formalin which comprises less than 0.001 percent by weight of divalent and/or polyvalent metal ions.

In both patent applications it is not described that besides HCl and formalin, the other starting materials of the MDA preparation, namely sodium hydroxide solution and aniline, can also likewise contribute to the phase separation problem and/or mulm formation. Furthermore, it is not described in the two patent applications whether the problems of phase separation can be solved by measures in the work-up.

If the formation of a mulm layer cannot be avoided completely, it will ultimately pass into one of the two phases. If the mulm layer enters the organic phase, this is less acceptable in the case of phase separation after the neutralization of the crude product than in the case of phase separation after the washing of the neutralized product. This is because in the case of the last-mentioned phase separation, not only do relatively large amounts of water, but naturally also the substances dissolved therein, such as e.g. NaOH and NaCl, then pass together with the mulm layer from the neutralization into the further processing steps where they may be troublesome, e.g. as a result of salt deposits in apparatuses and pipelines in the area of distillation. Even if the formation of a mulm layer (e.g. as a result of the measures described in EP 1 652 835 A1 and WO 2008/148631 A1) can be prevented, the organic phase obtained after phase separation can still comprise considerable fractions of aqueous constituents as disperse phase which, in further processing steps, can result in similar problems to an entrained mulm layer.

EP 2 103 595 A1 discloses in connection with the phase separation after the neutralization of the crude product that this phase separation can be assisted by adding water and/or aniline. Preferably, the reaction mixture diluted by adding water and/or aniline is separated into an organic and aqueous phase in Florentine flasks having plate packs supporting the coalescence of the two phases as internals (paragraphs [0043] and [0044]). In the case of phase separation after the washing of the neutralized product, with this procedure it is not possible to achieve completely satisfactory results because here, as explained above, the requirements placed on the quality of the phase separation are much higher. This was not acknowledged in EP 2 103 595 A1.

It would therefore be desirable to provide processing measures in order to be able to overcome this problem.

The quality of a work-up process for the preparation of MDA is defined on the one hand by the content in the product of undesired impurities which arise due to inappropriate purification steps. On the other hand, the quality of a work-up process is defined by the fact that the overall process can be operated without technical production failure.

Although the described processes of the prior art succeed in preparing MDA with a high yield, no technical auxiliaries are described which could improve the separation off of the aqueous constituents from the washed neutralization product with the desired effectiveness.

There was therefore a need for a process for the preparation of di- and polyamines of the diphenylmethane series in which it is possible, as a result of simple measures, to minimize the aqueous fractions of the organic phase obtained after phase separation of the washed crude MDA. This would improve the cost effectiveness of existing MDA processes.

SUMMARY

Taking into consideration that stated above, one subject matter of the present invention is a process for the preparation of di- and polyamines of the diphenylmethane series, in which a) aniline and formaldehyde are reacted in the presence of an acidic catalyst to give a reaction mixture comprising di- and polyamines of the diphenylmethane series, b) the reaction mixture comprising di- and polyamines of the diphenylmethane series is neutralized, c) the neutralized reaction mixture comprising di- and polyamines of the diphenylmethane series is separated in a separation container into an organic phase (1) comprising di- and polyamines of the diphenylmethane series and an aqueous phase, d) the organic phase (1) comprising di- and polyamines of the diphenylmethane series is further purified in a washing container with washing liquid, e) the mixture obtained in step d) is freed from aqueous constituents, giving an organic phase (2) comprising di- and polyamines of the diphenylmethane series, f) the organic phase (2) comprising di- and polyamines of the diphenylmethane series is freed distillatively from water and aniline, where for the separation off of the aqueous constituents in step e), the mixture obtained in step d)

e.1) is separated in a separating container into an aqueous and an organic phase (2a) still comprising residual amounts of aqueous constituents, and then e.2) the organic phase (2a) obtained in step e.1) (i) is passed through a filter bed made of coalescence fiber material and, ii) is then separated into an aqueous phase and the organic phase (2).

The invention also relates to a process for the preparation of di- and polyisocyanates of the diphenylmethane series in which di- and polyamines of the diphenylmethane series are prepared by the process according to the invention and are then reacted with phosgene to give the corresponding di- and polyisocyanates.

DETAILED DESCRIPTION

Embodiments of the invention are described in more detail below. Different embodiments here can be combined as desired with one another provided the opposite does not clearly arise for the person skilled in the art from the context.

The acid-catalyzed condensation of aniline and formaldehyde in step a) can be carried out by a process according to the prior art. In this, aniline and aqueous formaldehyde solution are preferably condensed at molar ratios in the range from 1.7:1 to 20:1, particularly preferably 1.7:1 to 5:1 in the presence of an acidic catalyst, preferably a strong mineral acid such as hydrochloric acid, upon use of preferably 0.001 to 0.9 mol of mineral acid per mole of aniline, particularly preferably 0.05 to 0.5 mol of mineral acid per mole of aniline. It is also possible to use solid acidic catalysts, as described in the literature. In this case, formaldehyde can be added to a mixture of aniline and acidic catalyst and the reaction solution can be fully reacted by stepwise heating. Alternatively, aniline and formaldehyde can also firstly be prereacted and then be admixed, with or without prior water separation, with the acidic catalyst or a mixture of further aniline and acidic catalyst, after which the reaction solution is fully reacted by stepwise heating. This reaction can be carried out continuously or discontinuously in accordance with one of the numerous processes described in the literature (e.g. in EP 1 616 890 A1 or EP 127 0544 A1).

In step b), the reaction mixture comprising the di- and polyamines of the diphenylmethane series is neutralized optionally with the addition of water and/or aniline. According to the prior art, the neutralization usually takes place at temperatures of, for example, 90° C. to 100° C. without the addition of further substances. However, it can also take place at a different temperature level in order e.g. to increase the rate of the degradation of troublesome byproducts. Suitable bases are, for example, the hydroxides of the alkali metal and alkaline earth metal elements. Preferably, aqueous NaOH is used. The base used for the neutralization is preferably used in amounts greater than 100%, particularly preferably 105% to 120% of the amount required stoichiometrically for the neutralization of the acidic catalyst used (see EP 1 652 835 A1). The pipeline between NaOH addition and neutralization reactor and/or subsequent phase separation apparatus is usually prepared from a material that is resistant to the reaction mixture. Additional protection of the pipeline can be achieved by inserting a Teflon inliner.

Then, in step c), the neutralized reaction mixture comprising the di- and polyamines of the diphenylmethane series is separated into an organic phase comprising di- and polyamines of the diphenylmethane series and an aqueous phase. This can be supported by the addition of aniline and/or water. If the phase separation is supported by adding aniline and/or water, then their addition preferably takes place already under intense mixing in the neutralization. In this connection, the mixing can take place in mixing sections using static mixers, in stirred-tank reactors or stirred-tank reactor cascades or else in a combination of mixing sections and stirred-tank reactors. A conductivity measurement with cut-off may be incorporated in the neutralization and washing in order to detect a phase reversal and to ensure the NaOH excess. The position in the separating containers can be controlled and monitored by means of a capacitive probe or by means of floats. The neutralized reaction mixture diluted by adding aniline and/or water is then preferably passed to an apparatus which, on account of its configuration and/or internals, is particularly suitable for separation into an organic phase comprising MDA and an aqueous phase, preferably phase separation or extraction devices corresponding to the prior art, as are described, for example, in Mass-Transfer Operations, 3rd Edition, 1980, McGraw-Hill Book Co, p. 477 to 541, or Ullmann's Encyclopedia of Industrial Chemistry (Vol. 21, Liquid-Liquid Extraction, E. Müller et al., page 272-274, 2012 Wiley-VCH Verlag GmbH & Co. KGaA, Weinheim, DOI: 10.1002/14356007.b03_06.pub2) or in Kirk-Othmer Encyclopedia of Chemical Technology (see "http://onlinelibrary.wiley.com/book/10.1002/0471238961", Published Online: Jun. 15, 2007, page 22-23) (mixer-settler cascade or settling container). Optimization of the residence time distribution in the separation containers of the neutralization and washing can take place by means of appropriate internals in the containers.

In step d), a washing of the organic phase with washing liquid, preferably water, follows. The mixture of organic and aqueous constituents obtained in the process is separated in step e.1) in a separating container into an organic phase comprising di- and polyamines of the diphenylmethane series (2a) and an aqueous phase in order to remove residual contents of salt (preferably as described in DE-A-2549890 on page 3). The phase separation in step e.1) leads to the fraction of aqueous constituents in the organic phase (2a) being less than 10% by mass, based on the total mass of (2a). The total mass of (2a) refers here to the sum of all constituents of the organic phase separated off from the aqueous phase in step e.1), i.e. organic constituents (which constitute the majority of (2a)), dispersed aqueous constituents and optionally entrained mulm layer.

In step e.2), the aqueous fractions of the organic phase (2a) obtained in step e.1) are separated off largely to completely. An excessively high water fraction in the organic phase, which is evident from clouding ("residual clouding") of this phase (dispersion of aqueous fractions in the organic phase), and/or an entrained mulm layer can have a disadvantageous effect on the further process steps as described above. An improvement in the MDA product quality can accordingly be achieved if the aqueous constituents can be separated off from the organic product phase. To achieve this through a second simple phase separation without further measures is unrealistic. In earth's stationary gravitational field, this could be made possible only as a result of a technically unreasonable separation time. This would accordingly require large technical apparatuses. Disadvantages include: a large quantity of liquid, increasing capital costs for apparatuses, required installation space, problems with building statics, etc.

According to the invention, the aqueous constituents are separated off from the organic phase (2a) by using a coalescence aid. According to the invention, the coalescence aid used is a filter bed of coalescence fiber material. The selection of fiber material is dependent, inter alia, on:
    wetting properties of the disperse phase (drops) on the fiber material,
    the interfacial tension of the substance system,
    the viscosity of both phases of the substance system.

The finely dispersed aqueous droplets must be able to wet the surface of the fiber material.

During passage of the liquid-liquid dispersion (aqueous constituents dispersed in the organic, MDA-containing phase (2a)) through the fiber material, the aqueous droplets present in finely dispersed form are able to wet the fiber surface. The aqueous droplets collect on the fibers (drop-fiber coalescence), after further fiber coating the distances between the positioned small droplets decrease, and finally the droplets combine to give larger drops (drop-drop coalescence). Upon exceeding a characteristic limiting drop diameter (dependent on the substance system, viscosity, flow conditions), the now-enlarged drops become detached as a result of the flow forces in the fiber bed and leave the fiber material as considerably enlarged drops compared to the incoming drops. On account of the improved sedimentation properties, these aqueous drops can be deposited in the following phase separation in the earth's gravitational field, which leads to a minimization of the residual cloudiness in the MDA product phase and to an improvement in product quality.

Success during the separation task depends on a formation of gas bubbles being avoided, which requires a process procedure at temperatures below the boiling point of the disperse system and the individual resulting phases and excludes the use of inert gases. Consequently, the separation task for the system according to the invention (step (e.2 (i)) is carried out in the temperature range preferably from 50° C. to 120° C., particularly preferably from 70° C. to 115° C. and very particularly preferably from 75° C. to 110° C. For the separation task, the pressure in the separating system is chosen such that boiling of the disperse system does not occur. The minimum pressure that is to be set depends on the temperature level and the composition of the disperse system and can be ascertained through simple experiments. Preferably, the separation task is carried out at atmospheric pressure ranging to an increased pressure of 10 bar absolute, preferably up to 5 bar absolute, particularly preferably up to 2 bar absolute.

The fiber diameter of the coalescence material is preferably from 1.0 µm to 150 µm, particularly preferably from 1.0 µm to 100 µm, very particularly preferably from 2.0 µm to 30 µm, with a nominal pore size of 5 µm to 40 µm being present at a fiber diameter of 2.0 µm to 30 µm, i.e. the fibers with a diameter of 2.0 µm to 30 µm are produced such that a pore size of 5 µm to 40 µm arises.

For separating off the aqueous droplets present in disperse form, use is made of fibers of water-wetting materials (e.g. glass or metal), preferably fibers made of a metallic material, particularly preferably fibers made of a metallic material which is resistant in the alkaline medium. Very particular preference is given to using a material made of stainless steel.

The specific hydraulic load upon passing the organic phase (2a) through the coalescence fiber material is preferably in the range $1.0\ m^3/(m^2h)$ to $10\ m^3/(m^2h)$, particularly preferably $1.0\ m^3/(m^2h)$ to $8.0\ m^3/(m^2h)$ and very particularly preferably $2.0\ m^3/(m^2h)$ to $6.0\ m^3/(m^2h)$.

The thickness of the filter bed according to the invention made of coalescence fiber material is preferably 1.0 mm to 100 mm, particularly preferably 1.0 mm to 50 mm and very particularly preferably 1.0 mm to 30 mm.

In step f), water and aniline are separated off by distillation from the organic phase comprising di- and polyamines of the diphenylmethane series obtained in step e.2 (ii)). This is preferably performed as described in EP 1 813 597 B1, particularly in paragraphs [0014] to [0043]. The organic phase obtained in step e.2 (ii)) preferably has a composition, based on the total mass of the mixture, of 5 to 10% by, mass of water and, depending on the feed ratios of aniline and formaldehyde, 5 to 90% by mass, preferably 5 to 45% by mass, of aniline and 5 to 90% by mass, preferably 50 to 90% by mass, of di- and polyamines of the diphenylmethane series. After emerging from the phase separation in step e.2), the organic phase comprising di- and polyamines usually has a temperature of from 50° C. to 150° C., preferably from 50° C. to 120° C., particularly preferably from 70° C. to 115° C. and very particularly preferably from 75° C. to 110° C.

The di- and polyamines of the diphenylmethane series obtained in this way can be reacted by the known methods with phosgene to give the corresponding di- and polyisocyanates of the diphenylmethane series. In this connection, the phosgenation can be carried out in accordance with one of the processes known from the prior art (e.g. DE-A-844 896 or DE-A-198 17 691).

If the aqueous fraction in the crude-MDA-containing organic phase is minimized after the separation container of the base washing (step e.1) via coalescence separation aid (step e.2), the following advantages result:
  i) The product quality is improved because more water is separated off from the organic phase and thus fewer salts remain in the crude-MDA-containing organic phase.
  ii) Energy costs are saved because less steam is required for the distillation of crude MDA because less water remains in the crude MDA-containing organic phase due to the improved phase separation.
  iii) Maintenance costs are saved since the fouling caused by salts in downstream apparatuses (e.g. evaporators, columns) is significantly reduced.

EXAMPLES

Example 1 (According to the Invention)

Crude MDA was prepared (step a) of the process according to the invention) by firstly reacting aniline and 30% strength formaldehyde (molar ratio 2.1:1) at approx. 95° C. to give the aminal. Following phase separation to remove the aqueous phase, the organic phase was admixed with 31% strength aqueous hydrochloric acid (degree of protonation 10%, i.e. 0.1 mol of HCl is added per mole of amino groups) and reacted at 50° C. to 150° C. in a reactor cascade. After complete reaction, the resulting reaction mixture was admixed with 32% strength sodium hydroxide solution in the molar ratio of 1.1:1 sodium hydroxide solution to HCl and reacted in a neutralization stirred container (step b) of the process according to the invention). The temperature was 115° C. The pressure was 1.4 bar.

The neutralizing base mixture was then separated in a neutralization separator into an aqueous, lower phase, which was passed to a wastewater collecting vessel, and into an organic phase (step c) of the process according to the invention). The aqueous phase had a pH of approx. 13, an NaCl content of approx. 17% by mass and an NaOH concentration of approx. 1.5% by mass, in each case based on the total mass of the aqueous phase. The organic, upper phase was passed to the washing (step d) of the process according to the invention). In a stirred washing container, the alkali MDA was washed with condensate. After separating off the washwater in a washwater separator (step e.1) of the process according to the invention) the crude MDA thus obtained was freed in step e.2) from further aqueous constituents and then pumped into a collecting vessel. The washwater separated off in step e.2 (ii)), which had a pH of approx. 11, an NaCl content of approx. 0.2% by mass and an NaOH concentration of approx. 0.8% by mass, in each case based on the total mass of the separated-off washwater, was pumped into a wastewater collecting vessel. The coalescence aid used in step e.2 (i)) was a coalescence filter made of metallic stainless steel fibers (material 1.4571). Its nominal pore size was 15 µm, and the fiber diameter was 10 µm. 11 superimposed, perfused fiber tiles were used. The flow rate was $4\ m^3/(m^2h)$, i.e. $4\ m^3/h$ throughput, based on a through-flow cross sectional area of $1\ m^2$. The organic phase obtained in this way was clear and had a water content of 7.0% by mass. Finally, in step 1), water and aniline are distilled off from the organic phase obtained in step e.2 (ii)), with MDA being obtained as bottom product.

Example 2 (Comparison)

The conditions were the same as in example 1, except that in this example step e.2) was not carried out. The organic phase obtained in this way was cloudy and had a water content of 7.9% by mass.

A comparison of example 1 with example 2 reveals that the use of a filter bed made of coalescence fiber material in step e.2) effectively reduces the water content and thus proportionately the impurities of residual salts, evident from the fact that the organic phase has no cloudiness and the water content is reduced according to analysis of the homogeneous soluble fraction.

The invention claimed is:

1. A process for the preparation of di- and polyamines of the diphenylmethane series, comprising:
   a) reacting aniline and formaldehyde in the presence of an acidic catalyst to give a reaction mixture comprising di- and polyamines of the diphenylmethane series,
   b) neutralizing the reaction mixture comprising di- and polyamines of the diphenylmethane series,
   c) separating the neutralized reaction mixture comprising di- and polyamines of the diphenylmethane series in a separation container into an organic phase (1) comprising di- and polyamines of the diphenylmethane series and an aqueous phase, d) further purifying the organic phase (1) comprising di- and polyamines of the diphenylmethane series in a washing container with washing liquid, e) freeing the mixture obtained in step d) from aqueous constituents, giving an organic phase (2) comprising di- and polyamines of the diphenylmethane series, and f) freeing the organic phase (2) comprising di- and polyamines of the diphenylmethane series distillatively from water and aniline, wherein the freeing of the aqueous constituents in step e) comprises:

e.1) separating the mixture obtained in step (d) in a separating container into an aqueous and an organic phase (2a), and then e.2) passing the organic phase (2a) obtained in step e.1) through a filter bed made of coalescence fiber material and then separating the organic phase obtained thereby into an aqueous phase and the organic phase (2).

2. The process of claim 1, wherein the fiber diameter of the coalescence fiber material is 1.0 μm to 150 μm.

3. The process of claim 1, in which the fibers of the coalescence fiber material are prepared from a water-wetting material.

4. The process of claim 3, in which the water-wetting material comprises glass or metal.

5. The process of claim 4, in which the water-wetting material is stainless steel.

6. The process of claim 1, in which the thickness of the filter bed of coalescence fiber material is 1.0 mm to 100 mm.

7. The process of claim 1, in which the step of passing the organic phase (2a) through a filter bed made of coalescence fiber material is carried out in the temperature range from 50° C. to 120° C.

8. The process of claim 2, wherein the fiber diameter of the coalescence fiber material is 1.0 μm to 100 μm.

9. The process of claim 8, wherein the fiber diameter of the coalescence fiber materials is 2.0 μm to 30 μm.

10. A process for preparing di- and polyisocyanates of the diphenylmethane series comprising phosgenation of a di- and/or polyamine of the diphenylmethane series, wherein the di- and/or polyamine of the diphenylmethane series is prepared by the process of claim 1.

* * * * *